United States Patent [19]

Strickman et al.

[11] 4,311,543
[45] Jan. 19, 1982

[54] METHOD OF MANUFACTURING A DISPOSABLE CONTRACEPTIVE INTRAVAGINAL CERVICAL BARRIER

[76] Inventors: Robert L. Strickman, Lawrence Rd., R.D. 1, Bridgeton, N.J. 08302; Erick-Pierre Fournier, 30 Park Ave., New York, N.Y. 10016; Melvyn B. Strickman, Lawrence Rd., R.D. 1, Bridgeton, N.J. 08302

[21] Appl. No.: 111,266

[22] Filed: Jan. 11, 1980

Related U.S. Application Data

[62] Division of Ser. No. 924,971, Jul. 17, 1978, Pat. No. 4,198,965.

[51] Int. Cl.³ .................. B32B 5/18; B29D 27/04; A61F 5/46
[52] U.S. Cl. .................. 156/224; 128/127; 156/245; 156/308.2; 264/45.5; 264/46.4; 264/46.6; 264/321
[58] Field of Search .................. 264/54, 51, 321, 129, 264/45.5, 46.4, 46.6; 128/127; 156/224, 245, 308.2

[56] References Cited

U.S. PATENT DOCUMENTS

| | | | |
|---|---|---|---|
| 3,039,911 | 6/1962 | Fox | 156/224 |
| 3,144,372 | 8/1964 | Peterson et al. | 264/321 X |
| 3,170,178 | 2/1965 | Scholl | 264/321 X |
| 3,234,065 | 2/1966 | Best | 156/224 |
| 3,244,571 | 4/1966 | Weisman | 264/321 X |
| 3,396,062 | 8/1968 | Waite | 156/245 |
| 3,463,745 | 8/1969 | Hofrichter et al. | 128/127 X |

FOREIGN PATENT DOCUMENTS 54-158471 12/1979 Japan .................. 156/224

OTHER PUBLICATIONS

Zwolinski, Leon M., "Molded Integral-Skin Urethane Foam," In SPE Journal, Sep. 1969, vol. 25, pp. 24-27.

*Primary Examiner*—Philip Anderson
*Attorney, Agent, or Firm*—Duffield & Lehrer

[57] ABSTRACT

Disposable contraceptive intravaginal cervical barriers of one, two, three, four, or five layers in the form of standard pessaries with at least one layer impervious to the passage of sperm, with a medicament such as spermicide, germicide, or an abortion inducing agent either impregnated into a foam plastic layer or in the form of a layer of gel or powder, said medicament being activatable upon contact with an aqueous solution.

Methods of producing disposable contraceptive barriers either as a wet foam plastic method wherein medicament is added to liquid foam and the resulting mixture is formed in a mold with any subsequent layers then added, or as a dry foam plastic method wherein layers including a layer of medicament in the form of a gel or a powder are superposed in sequence and formed in a die.

12 Claims, 16 Drawing Figures

METHOD OF MANUFACTURING A DISPOSABLE CONTRACEPTIVE INTRAVAGINAL CERVICAL BARRIER

This is a division of application Ser. No. 924,971, filed July 17, 1978, now U.S. Pat. No. 4,198,965.

BACKGROUND OF THE INVENTION

The present invention relates to the manufacture of disposable contraceptive intravaginal barriers. It also relates to the methods for making these disposable barriers.

Recent incidence of complications with the intrauterine device (IUD) and the contraceptive pill has led women throughout the world to revert to reusable cervical contraceptive pessaries such as the diaphragm and other related cervical pessaries such as the cervical cap, the vault cap, and the vimule. These pessaries, although not as effective as the IUD and the pill preventing pregnancy, have shown no adverse physiological or systemic effects.

Currently available cervical pessaries such as the diaphragm and related cervical pessaries are generally made in the form of a soft rubber cap with a metal spring embedded in the rim. These pessaries present certain disadvantages that operate to discourage their widespread use. Some of these disadvantages are as follows: their effectiveness is substantially lower than the pill, the IUD, and injectable hormones; prior to insertion they must be coated with spermicidal foam or jelly; after use they must be cleaned and properly stored (this requirement discourages their use especially in areas of the world where water is not readily available); and, because of the cost of spermicides, cervical pessaries can become expensive if used frequently.

The present invention provides a method of manufacturing a disposable cervical barrier that eliminates the disadvantages of currently available cervical pessaries. It provides a method of manufacturing a disposable cervical barrier made chiefly of plastic foam, preferably polyurethane foam, that is preimpregnated with medicament, such as spermicide, germicide, or an abortion inducing agent, that is activated by contact with a small amount of water or any aqueous solution, including internal secretions. Thus, preparation is made easier and preparation time shorter, factors that encourage the use of the present device. In addition, this disposable pessary approaches the effectiveness of the pill.

The medicament can also be "time encapsulated" so that it is activated for a preset time period upon contact with an aqueous solution.

The present invention also relates to two methods for making these disposable barriers.

A conventional assembly procedure to produce a finished pessary from open cell bulk form would have to follow a number of labor intensive and time consuming steps in the following general sequence: One: cutting two parallel blocks of foam; two: machining the blocks into two mating half hollow spheres; three: coating the mating sides of said half spheres with some impermeable viscous medium such as latex; four: assembling the two matching parts for adhesion and curing; five: cleaning and neutralizing the foam assembly; six: dip saturation of the polyurethane foam elements with a suitable concentration of spermicides; and seven: sterilization of the finished article and packaging.

Two efficient and labor saving methods of making disposable pessaries are described here. One method is a "wet foam," or "quick foam," technology that utilizes a method of adding the medicament to liquid plastic foam, preferably polyurethane foam. This would require only one, two, or three steps, depending on the number of protective layers required in the cervical barrier.

SUMMARY OF THE INVENTION

It is accordingly a primary object of the present invention to provide a method of manufacturing disposable cervical pessary device and a method of producing the same that will avoid the above drawbacks of present contraceptive devices.

It is thus an object of the present invention to provide a method according to which a disposable contraceptive intravaginal cervical barrier can be produced that has a foam plastic member that is impregnated with a medicament such as spermicide, germicide, or an abortion inducing agent that is activatable upon contact with an aqueous solution.

It is also an object of the present invention to provide a method according to which a disposable contraceptive intravaginal barrier can be produced that has a layer of medicament in the form of a gel or a powder, such as spermicide, germicide, or an abortion inducing agent that is activatable upon contact with an aqueous solution.

It is further an object of the present invention to provide a method of manufacturing a pessary according to which the medicament is time encapsulated for a preset time release period.

It is a further object of the present invention to provide a device and a method according to which a disposable pessary can be produced in the form and shape of any known intravaginal cervical barrier such as the diaphragm, the vimule, the vault cap, or the cervical cap.

It is a further object of the present invention to produce a disposable cervical barrier with one, two, three, four, or five separate layers.

It is another object of the present invention to produce a disposable pessary in which the rim of the pessary contains a flexible means to produce a spring-tension effect for better holding within the vagina.

It is another object of the present invention to provide a method according to which the disposable pessary can be produced by a wet foam technology, wherein the medicament is added to wet plastic foam and mixed and the resulting mixture formed in a mold.

It is yet another object of the present invention to provide a method according to which the disposable pessary can be produced by a dry foam technology, wherein dry barrier layers and a layer of medicament in the form of a powder or a gel are laid one upon the other in sequence and formed in a die to the shape of a pessary.

BRIEF DESCRIPTION OF THE DRAWINGS

The invention is illustrated by way of example in the accompanying drawings, which form a part of this application, and in which.

DETAILED DESCRIPTION OF THE INVENTION

Figure 1:
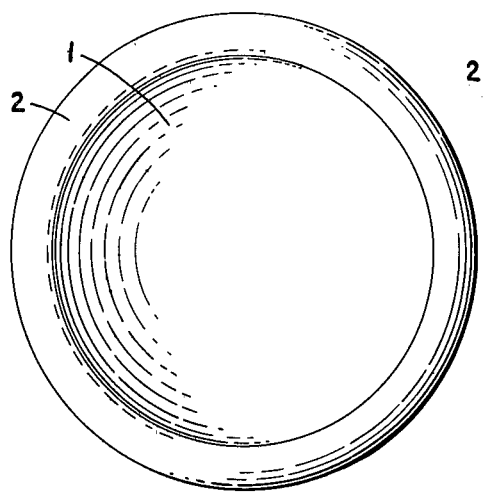
FIG. 1 is a top view of a one member pessary.
Figure 2:
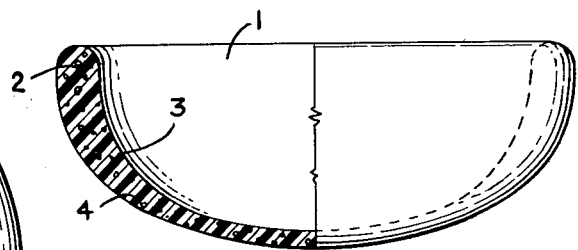
FIG. 2 is a side view with a quarter section of FIG. 1

FIGS. 1 and 2 illustrate one of several structural arrangements that can be assumed by the present device. The figures show a unitary cervical pessary member 1 made entirely of foamed plastic material, preferably polyurethane. The member shown has an approximately circular rim 2 and is approximately hemispherical with a hollow, or dished center, but this construction can be altered to conform to various configurations. A one time use contraceptive cervical barrier made of foamed plastic, preferably polyurethane, can ussume any of the standard shapes currently made of rubbery material, including the vault cap, the diaphragm, the vimule, and the cervical cap.

The vault cap, sometimes called the Dumas cap, is made of rubber or plastic and is shaped like a circular bowl with a thick rim and thin center. It clings by suction to the vault or roof of the vagina, following the contour of the cervix.

The diaphragm is held in place by the spring tension of the rim, the woman's vaginal muscle tone, and the pubic bone.

The cervical cap, unlike the diaphragm, which blocks the entire upper part of the vaginal canal, blocks only the cervix. It is in shape a small, thimble-shaped cup and is held in place by suction rather than by spring tension.

The vimule cap, or vimule, combines the characteristics of the vault cap and the cervical cap. Like the vault cap, it is made of thick rubber or plastic; like the cervical cap, its dome is deep and fits closely against the cervix. Unlike either, however, the vimule adheres with a very strong suction because a flanged rim permits the device to be pressed more firmly onto the roof of the vagina.

Member 1 is made of flexible foam plastic, preferably polyurethane foam, preimpregnated with medicaments that can be spontaneously activated upon contact with a small amount of water or any aqueous substance. The medicaments can include spermicide, germicide, or an abortion inducing agent such as prostaglandin (PGE$_2$). In addition, the medicaments may be "time encapsulated" for any particular "time release" effect, as for example up to 48 hours maximum protection after activation upon contact with an aqueous substance.

In order to present a physical barrier to the passage of sperm, internal side 3 can be cured in the process of manufacture so as to present an impermeable barrier to the passage of sperm. Alternatively, external side 4 can be cured to present a similar impermeable barrier to the passage of sperm. Either side 3 or side 4 remains porous so as to allow free interaction with the medicaments.

Rim 2 can be cured during the course of manufacture so that it obtains the resilient tension of a spring, so that it can be of aid in maintaining the pessary in position in the vagina.

Figure 3:
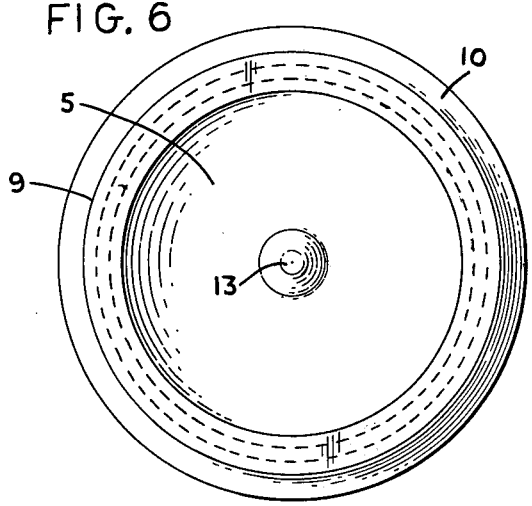
FIG. 3 is a top view of a two layer pessary.
Figure 4:
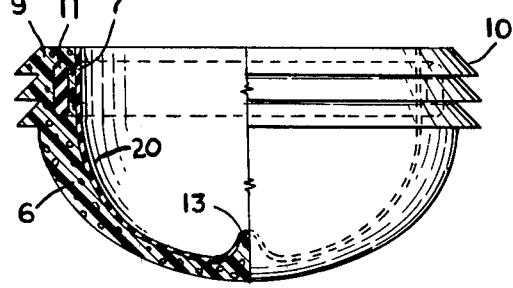
FIG. 4 is a side view of FIG. 3 with a quarter section showing a two layer pessary with a foam plastic outer layer.
Figure 5:
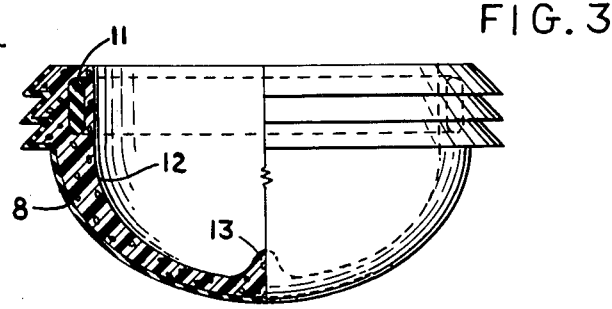
FIG. 5 is a side view of FIG. 3 with a quarter section showing a two layer pessary with a foam plastic inner layer.

FIGS. 3, 4, and 5 illustrate a second embodiment similar in general configuration to the first embodiment of FIGS. 1 and 2. Cervical pessary member 5 comprises plastic foam portion 6, made preferably of polyurethane foam, and internal film 7, impermeable to the passage of sperm. Foam portion 6 and film 7 are integrally joined, that is, film 7 adheres to portion 6. Alternatively, external film 8, similarly impermeable to the passage of sperm, is illustrated in FIG. 5. Film 7 and film 8 are made preferably of latex, plastic, or natural rubber. Substantially circular rim 9 is equipped with circumferential gripping means of ridges 10 that are integral with foam layer 6 in FIG. 4 and with film layer 8 in FIG. 5. These ridges are shown with three superposed ridges but one, two, or more than three may be used. These ridges are designed to aid in maintaining cervical pessaries of certain configurations, such as the vault cap, in proper position. The ridges are by way of illustration only, and any aid in gripping can of course be substituted or eliminated. These or similar aids may of course be used in conjunction with member 1 of FIGS. 1 and 2.

This construction also comprises optional flexible resilient ring 11 embedded within the rim. In both FIGS. 4 and 5 ring 11 is independent of latex films 7 and 8. The ring is shown as flat by way of illustration, but can be of any other shape. This flexible ring has the resilience of an internal spring to aid in keeping the pessary in place. It can of course be eliminated, and rim 9 can be cured during the course of manufacture so that it obtains the resilient tension of a spring, similar to rim 2 of FIGS. 1 and 2. This resilient ring is particularly useful in the pessary constructions that are held in the vagina by tension or aided by tension.

Ring 11 can of course be included in unitary pessary member 1 of FIG. 1 and 2.

The two-layer embodiment of FIGS. 3, 4, and 5 is shown with a substantially circular rim and is half hemispherical in vertical view with a hollow center by way of illustration only, and it is understood that it can be adapted for use as any related intravaginal cervical pessary, including a diaphragm vault cap, vimule, or cervical cap.

Foam portion 6 is made of flexible foam plastic, preferably polyurethane foam, preimpregnated with medicaments that can be spontaneously activated upon contact with water, as described above in reference to the first embodiment. Similarly, the medicaments can include spermicides, germicides, or an abortion inducing agent. Also, the medicaments may be time encapsulated.

Optional protrusion 13 is formed integral with internal side 12 at the center of the pessary. Protrusion 13 is designed to assume close contact with the opening of the cervix for added protection against the passage of sperm. This option feature would be especially desirable in the vault cap pessary construction. Optional protrusion 13 could of course be an optional feature for the first embodiment illustrated in FIGS. 1 and 2.

Figure 6:
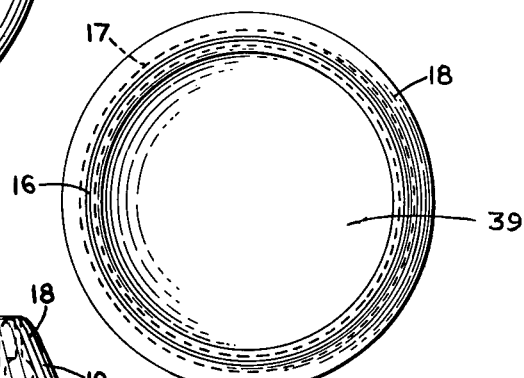
FIG. 6 is a top view of a three layer pessary.
Figure 7:
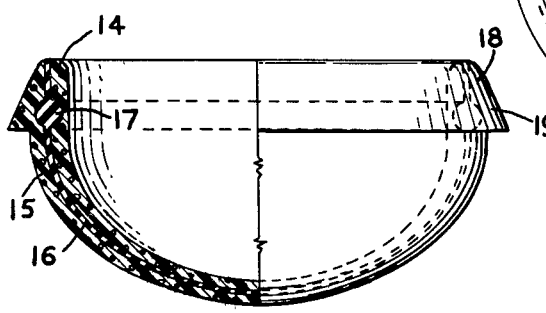
FIG. 7 is a side view of FIG. 6 with a quarter section showing a three layer pessary.

FIGS. 6 and 7 illustrate a third embodiment of an intravaginal cervical barrier 39. This construction is three layered, with plastic foam layers 14 and 15. These two foam layers are distinct types of foam. They are in intimate contact with, or sandwich, a thin barrier of flexible sperm impermeable film barrier 16 such as latex.

Integral with film barrier 16 is optional ring 17, preferably a latex O-ring, situated inside the rim section and designed to be compressed into the vaginal vault. This substantially stretchable yet resilient material is particularly useful in the pessary constructions that are held in the vagina by tension or aided by tension.

Alternatively, rim 18 can be cured to a resilient spring tension in a similar manner to rim 2 as described in the first embodiment.

In addition to the mechanical barrier 16 impervious to the passage of sperm, this embodiment has the advantage of having two separate layers impregnated, as described in the prior two embodiments, with therapeutic ingredients, or or medicaments, which can be spontaneously activated by a small amount of water or any other aqueous solution such as internal body secretions and so on. The external layer of foam, that is, layer 15, particularly could incorporate a combination of both spermicides and a germicide to combat potential venereal invasion. The internal side could be suitably impregnated with spermicides. An abortion inducing agent, as described relative to the first two embodiments, could be included among the medicaments. As described previously, the medicaments can be time encapsulated.

Another advantage of this construction is that, in addition to their ability to relase complementary therapeutic ingredients, one of the foam layers (preferably external layer 15) can be formulated in such a way as to have a "swelling coefficient" substantially higher than adjacent foam layer 14, with the result of a highly desirable expansion of the contraceptive barrier against the vaginal walls.

In addition, the device can optionally be equipped with a protruding circumferential ridge 19 integrated to the foam layer 15, which, in combination with the swelling action of the rim 18, is designed to maintain the pessary in its proper position. Alternatively, such a circumferential gripping provision can assume the form of a plurality of superposed ridges 10 as shown in FIGS. 3, 4, and 5. This construction is by way of illustration only, for it is apparent that other gripping means are possible.

Protrusion 13 as described in reference to FIGS. 4 and 5 can of course be optionally constructed at the center of internal side 20.

The manufacturing process for the three embodiments involves a "quick polyurethane foam," or "wet foam" technology, which not only allows virtually any shape to be "mold coated" in either a one-, two-, or three step operation, depending upon the desired number of protective layers required in the cervical barrier, but which prevents the therapeutic ingredients, namely spermicide, germicide, or an abortion inducing agent, admixed into the foamable solution from becoming inactive in the process. While this technique lends itself remarkably well to a fully automated manufacturing operation of relatively low capital investment, it also permits the achievement of an attractively low production cost.

In the case of a cervical barrier made entirely of foam, the only operation required is to pour the foamable mixture including the spermicidal and other therapeutic ingredients into a dished mold and to let it cure therein, allowing one side of the pessary to develop an impermeable skin while leaving the other side permeable to allow contact with the medicaments. Thus only one manufacturing step is required prior to sterilization and packaging.

In the case of a double layered construction incorporating an intermediate mechanical barrier, two steps are required: first, pouring foamable polymer into a dished mold and allowing it to cure; second, spraying or coating said polymer with a film of liquid latex.

In the case of a triple layered construction, a third step would be required, namely, after curing, pouring the second half of the foamable polymer over the foregoing two-layered construction. After curing and sterilization, the final article is ready for packaging.

The significantly shortened production cycle allowed by the present wet foam technology process permits substantially lower production cost over existing rubber pessaries. This, in turn, allows them to belong to the "disposable" category in view of their correspondingly low retail cost.

As noted above, the manufacturing process in the present invention not only allows virtually any shape to be mold-coated but also permits the imparting to the foam design features heretofore impossible to obtain by conventional hot knife machining methods.

Various intravaginal cervical barriers are possible utilizing the embodiments described here. For example, the wall thickness of the diaphragm is uniform and should preferably not exceed 3/32 of an inch. The diaphragm particularly should optionally include a circumferential O ring of stretchable yet resilient material in order to allow proper fitting between the posterior aspect of the pubic bone and the posterior vaginal fornix. Rings of other cross sectional shapes may, of course, be used just as effectively, such as flat ring 11 in FIGS. 4 and 5, or a half moon or bone shaped configuration.

The spring tension effect created by a circular coil or latex O ring could be alternately achieved by precise curing of the rim section to the exclusion of the rest of the device; in so doing, some desirable degree of resiliency can be developed, eliminating the necessity of adding a ring of the internal structure of the device to achieve compressive action, particularly on a one time use basis.

The vault cap, which has been described, generally assumes the shape of a circular bowl. It operates by suction. It is characterized by a thick rim progressively diminishing to a relatively thin center in the order of no less than ⅛ of an inch.

The vimule is shaped in the form of a deep, double dome like structure and includes a flanged rim designed to permit the device to be pressed firmly onto the roof of the vagina.

The cervical cap comprises a small, thimble shaped cup designed to block the cervix. It is held in place by suction only.

Alternately, suitable disposable cervical contraceptive barriers could be made with a slightly modified yet significantly different construction by using a thermoforming or dry foam process.

The structured cross section of a typical contraceptive barrier made by this technique could comprise either three, four, or five separate layers.

Figure 8:
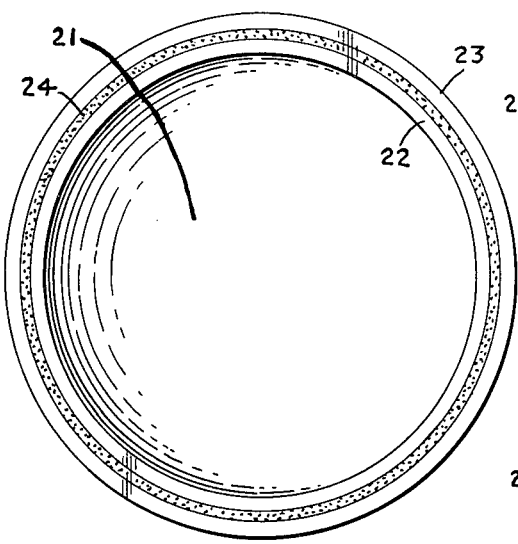
FIG. 8 is a top view of a pessary that can have one, two, three, four or five layers.

The top view of each of these embodiments would be similar and is shown in FIG. 8 as thermoformed pessary 21. In external construction, the thermoformed pessaries would follow the constructions described for the various types of intravaginal cervical barriers shown in FIGS. 1 through 7, namely, a diaphragm, a vault cap, a vimule, and a cervical cap, together with all the optional variations described there.

Figure 9:
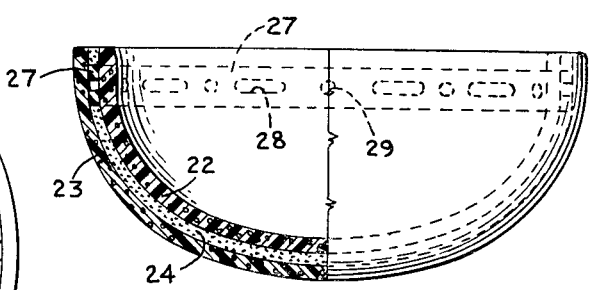
FIG. 9 is a side view of FIG. 8 with a quarter section showing a three layer pessary.

FIG. 9 illustrates a quarter section of a three layer construction formed by thermoforming or the dry foam process, as compared to the wet foam process previously described. Plastic foam layer 22 forms the inner layer of pessary 21, shown as a hollow hemisphere, but with the understanding that this is for purposes of illustration only and can be adapted to other intravaginal cervical barriers. Plastic foam layer 23 forms the outer layer of the pessary. In intimate contact with both layers, or sandwiched between the layers, is a layer of medicaments 24, consisting of spermicides, germicides, or an abortion inducing agent, in the form of a gel with a desirable thickness of ½ to 1 millimeter, depending upon the desired degree of concentration. As in the wet foam process, the plastic is preferably polyurethane.

While the medicaments can be easily handled in such a way through the manufacturing process, they can be spontaneously activated at the contact of tap water or any aqueous solution just prior to insertion or just prior to packaging. As they liquify, the medicaments permeate evenly throughout the two layers of polyurethane foam and are held between the open cells. Lowermost section 23 of foam should be desirably cured in such a way that the cells become progressively closed. Bottom surface 23 constitutes a totally impermeable barrier against the passage of sperm from the outside and against the seepage and loss of the medicaments to the outside of the contraceptive barrier.

Figure 10:
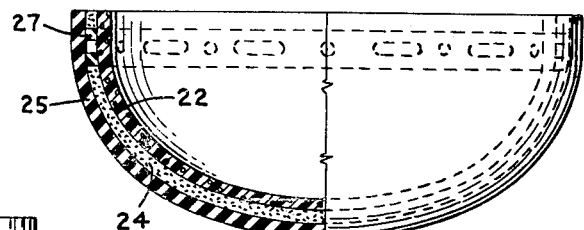
FIG. 10 is a side view of FIG. 8 with a quarter section showing a variation of a three layer pessary.

FIG. 10 is a quarter section illustration of a variation of the three layer construction. Here inner foam layer 22 and medicament layer 24 remain as in FIG. 9, but film layer 25 is placed as the outer layer rather than foam layer 23. Film layer 25 is preferably a highly pliable, resilient film of plastic, preferably polymeric, material that acts as a protective barrier against the diffusion of spermicides into the lower layer of polyurethane foam 22 and as a barrier against the penetration of sperm from the outside. As long as such a barrier is thermoformable, a wide variety of polymeric compositions is deemed suitable, such as natural rubber, latex, polyethylene, polypropylene, polyester, or any number of commercially available coextruded or laminated films.

Figure 11:
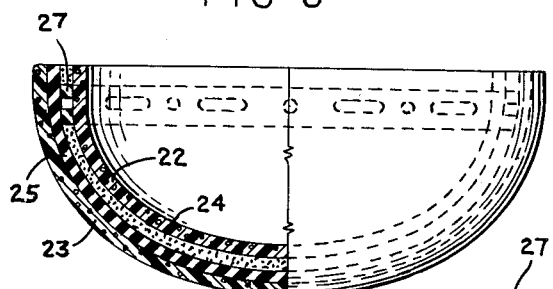
FIG. 11 is a side view of FIG. 8 with a quarter section showing a four layer pessary.

FIG. 11 is a quarter section of FIG. 8 illustrating a four layer construction. Here a combination of FIGS. 9 and 10 is shown. That is, protective film layer 25 is added to FIG. 8 between layers 23 and 24, or, in another sense, foam layer 23 is added as an outer layer to FIG. 10.

Figure 12:
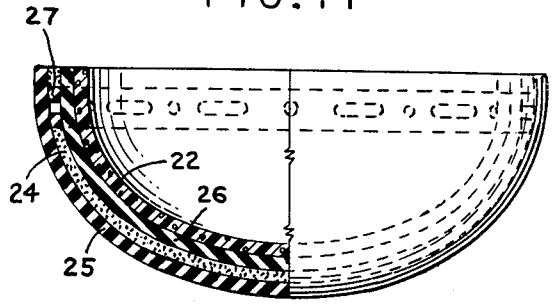
FIG. 12 is a side view of FIG. 8 with a quarter section showing a variation of a four layer pessary.

FIG. 12 is a quarter section of a second four layer construction. Substantially flexible top film layer 26 is placed in intimate contact with, that is, is sandwiched between, layer 24 and layer 22. Layer 24 of medicament is then sandwiched between film layers 25 and 26. The top layer of resilient film 26 can be of various kinds in order to allow contact with the water and the medicament for activation, that is, be permeable to water. First, layer 26 can be water soluble. Second, layer 26 can incorporate a plurality of mechanically induced perforations, or tiny holes, to let the water go through. Third, layer 26 can be simply permeable to water simply by virtue of its molecular structure.

Figure 13:
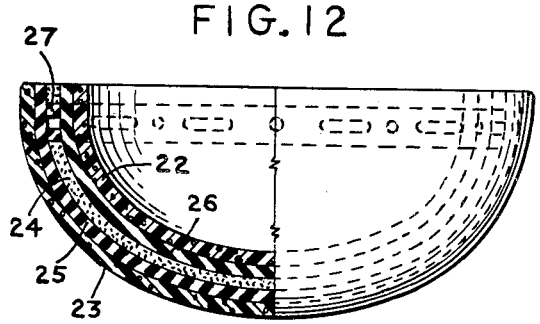
FIG. 13 is a side view of FIG. 8 with a quarter section showing a five layer pessary.

FIG. 13 is a cross section of FIG. 8 illustrating a five layer construction. Essentially, it is FIG. 12 with foam layer 23 added as the outside layer to form the fifth layer.

Figure 14:
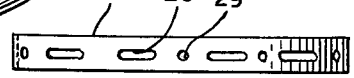
FIG. 14 is side view of a flexible ring.

FIG. 14 illustrates a side view of plastic ring 27, which is shown in cross section in FIGS. 9, 10, 11, 12, and 13. These contraceptive barriers each incorporate around their rims flat, resilient, plastic ring 27, which optionally forms a series of spaced perforations 28 and 29. These perforations are shown elongated and circular for purposes of illustration only and can assume a number of varied configurations. Ring 27 is shown in FIG. 9 sandwiched between and joining plastic foam layers 22 and 23, in FIGS. 10 and 11 sandwiched between and joining foam layer 22 and film layer 25, and in FIGS. 12 and 13 sandwiched between and joining film layers 25 and 26. Perforations 28 and 29 are designed to allow the layers bordering the plastic ring to be heat sealed together through the ring and to permit these three elements to be locked or bound to each other permanently. In effect, the layers bordering the ring are to be fused to each other through holes 28 and 29 of the ring.

Figure 15:
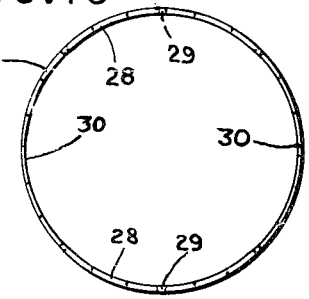
FIG. 15 is a top view of the flexible ring.

In order to fold the device in half to facilitate insertion into the vagina, ring 27 can incorporate two diametrically opposed thin points 30 as shown in the top view in FIG. 15. There is of course no restriction to the types of contraceptive barriers that such a structure can be adapted to, that is, it can be applied to a diaphragm, a vimule, a vault cap, or any other medically acceptable intravaginal cervical barrier. The ring can be of any type of flexible and resilient material as long as the proper spring tension can be obtained economically and maintained for the purpose of holding the pessary over the cervix for a one time application.

In the interest of better material handling as well as the elimination of possible adverse effects caused by the combination of pressure and heat exerted by the thermoforming dies, an alternate construction is possible.

Instead of a gel, the layer of medicament can be in the form of a powder or be dehydrated after being applied as a gel. It can also be applied in any fashion. For example, it can be sprayed, or jet sprayed, in liquid or dry form, on a plastic film substratum. This is provided, of course, that the dry layer 15 be readily soluble on contact with water for activation. The general embodiment would be the same as for FIGS. 8, 9, 10, 11, 12, 13, 14, and 15. The powder would lend itself to improved handling over a layer of gel, whose uniformity might be adversely affected during thermoforming.

It is noted that FIGS. 9 through 13 can be adapted to include the gripping means 10 and 19 shown in FIGS. 4 and 7 and protrusion 13 shown in FIG. 4.

The medicament, whether gel or powder, can be time encapsulated for any time release effect in the same manner as described for FIGS. 1 through 7.

Figure 16:
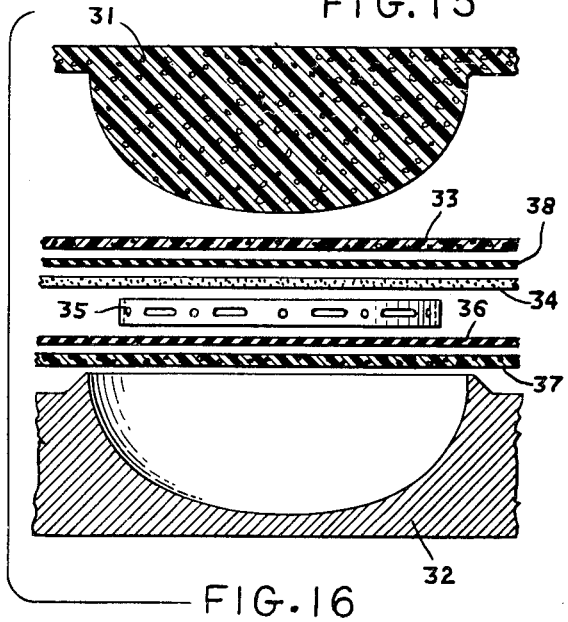
FIG. 16 is a side view showing pessary layers in superposition between a male die and a female die.

With regard to the manufacturing of the foregoing thermoformed articles, the various components are assembled and superposed one above the other before being placed between thermoforming male die 31 and female die 32 as illustrated in FIG. 16. The structural elements of the contraceptive barrier illustrated in FIG. 13 include from top to bottom in sequence: inner foam layer 33, preferably polyurethane foam; layer 34 of medicated gel or powder; plastic ring 35; optional layer 36 of polymeric film impermeable to the passage of sperm; and bottom layer 37 of plastic foam, preferably polyurethane. Optional film layer 38 as illustrated in FIGS. 12 and 13 can of course be inserted between layers 33 and 34 if a five layer pessary is desired. Likewise, either layer 36 or layer 37 can be optionally withdrawn to make a three layered pessary.

As all of the aforementioned components, except for the plastic ring, are readily thermoformable under a specific temperature range, any die in combination with moderate heat will impart to these materials any desired permanent shape. The components of the desired type of pessary are positioned in parallel arrangement between two mating dies. One male die is in the form of a convex punch and one female die is in the form of a reciprocal cavity. As the two heated dies move closer to each other, the polymeric layers become permanently set in the form of a generally hollow shape.

As part of the thermoforming mold, provisions are also made for a circular cutting edge and for an integrated thermal sealing attachment, such as a generator of high-frequency radio energy to weld together the ring and the two foam layers.

With these two added attachments, thermoforming, cutting, and sealing of the article can be effected sequentially in a one step operation that lends itself to fast production cycles and low cost per unit.

After quality control and sterilization, the one time use article can be suitably folded in half along its length, premoistened if so desired (therefore ready for insertion), and packaged in an air tight plastic laminated aluminum foil pouch. The ability of such a disposable contraceptive barrier to be folded and packaged in an unobstructive way presents a major advantage for the consumer over conventional types that have to be stored flat in a horizontal position.

The preparation of preimpregnated disposable contraceptive intravaginal cervical barriers, manufactured from polyurethane compositions with various additives distributed throughout the urethane has been discussed.

The contraceptive compositions are introduced at a point during the manufacturing of the foaming polymeric compositions. In the process, the spermicidal, or contraceptive compositions or formulations can be incorporated as a solid, liquid, cream or ointment, which can be water soluble, partially water soluble, or water insoluble, but is capable of being carried out of the foam by compression and release. These diaphragm barriers can be made with a variety of spermicidal agents.

Typically, polyurethane flexible foams cannot withstand reactive additives which are not normally a component of the system being foamed. What usually occurs is that the foam will collapse, bubble, sometimes smolder due to the generation of heat.

Certain reactive materials can be introduced without destroying the foam structure which is useful as a diaphragm. To disperse the spermicidal compositions homogeneously within a foaming polyurethane mass it is necessary to introduce and blend these substances in such a way that the composition undergoing foam formation is protected from the foam depressing effects of the additives. In the manufacture of these contraceptive devices, additives are introduced at a specific time during the reaction in such a way that the foaming action initiated by the urethane polymer chemical reactions are not interfered with. This process works because the catalyst and resin ingredients are allowed to react initially before the addition of the spermicidal ingredients. The spermicidal compositions are added after the initial reaction, but before the foaming reaction has proceeded beyond the stage where further mixing is possible.

A urethane supporting skeleton having a cell structure ranging from unicellular (closed) to multicellular (open) characteristics as well as combinations of both of these characteristics is achieved. The urethane comprises a cellular matrix enveloping the additives within individual cells and in the cellular walls.

The additive ingredients carried integrally by the urethane composition are available when required and activated. The ingredients are carried in such a way that their release is made possible by a squeezing compression effect, and or when water or other fluids entering the cellular structure contact the additive ingredients. Some of the active ingredient particles are held loosely within the cells. The water serves to release these ingredients as soon as contact takes place. Other ingredient particles are held between the cells, actually enveloped by the walls of the cells. Water contacting the composition does not engage these particles quite so readily. However, upon squeezing the product and deforming the cell structure mechanically, the water is made to reach these enveloped ingredients. The composition has the "memory of a natural sponge" and returns to its original shape after being squeezed. This characteristic allows shaped articles made from these compositions to be inserted and removed from body cavities having various anatomical configurations quite easily.

The water, or other liquids, such as internal body fluids, such as internal secretions of the vaginal walls, flows from cell to cell, filling each cell and spilling outward to the adjacent cells. In addition, diffusion of the fluids takes place through the cell walls themselves forming the interstitial matrix. The water, or fluids causes these spermicidal ingredients to flow outward the outer surfaces of the article where they flow onto and contact the inner body cavity surfaces for which intended. Squeezing and release facilitates this process greatly.

Release can be controlled not only by varying solubility rates of the ingredients, but by varying particle size, emulsification techniques, and by a combination of the above.

This product, containing a polyurethane component, combined with various active ingredients meets the requirements of a dispensing package. It holds the spermicide compositions until use is desired, in a stable form, both chemically, and physically. It then serves to dispense as needed by releasing its contents.

As opposed to filling a package whereby the walls serve as an outer boundary, this product defines a package where the ingredients and the container boundaries are coextensive with each other, forming "micro-packages" of ingredients homogeneously dispersed within a container. These "micropackages" form aggregates which collectively comprise a dispenser for the spermicide.

With regard to the previous indications of time encapsulated medicament, an example of time encapsulation or microencapsulation is described as follows:

Step I

Microcapsules of oils or silicone components are prepared as follows: 1100 grams of gelatin are dissolved in 1.8 liters of water. The water temperature is brought to not more than 54° to 55° C. 1000 grams of gum arabic are dissolved in 1.8 liters of hot water under the same condition.

Step II

The warm solutions from Step I are mixed in a suitable container and heated to exactly 55° C. The solution is stirred and the pH value adjusted to 4.65 by the addition of either 0.1 N NaOH or 0.1 N HCl.

Step III

Oil fractions are added as follows: 9 kilos of isopropyl palmitate are added to the mixture with vigorous stirring, the mixture is cooled slowly with stirring, and the mixing is continued until the temperature reaches 10° C.

Step IV

The microcapsules are separated from the aqueous solution and dried by treatment with suitable solvents. The size distribution of the microcapsules is determined by the speed by stirring, by the amount of oil, and by the microcapsules' wall components.

The preparation of premedicated material manufactured from polyurethane compositions is described as follows:

The medicament or treatment chemicals are introduced at a point during the manufacture of the polymeric material.

In the process, the medication can be incorporated as a solid, liquid, or ointment. The amounts can range from low to high concentrations and can be precisely controlled to yield a prescribed dose of medicament as the pessary is used.

formulations can be made for single wall or double wall cervical barrier as listed below:

I. Single wall spermicidal composition (Column 5 ingredients)
   Resin F-202 prepolymer: 10 gm
   Catalyst: 0.25 gm
   Dodecaethyleneglycol monolaureate: 0.80 gm
II. Single wall spermicidal composition (Column 12 ingredients)
   Hypel 2001: 10 gm
   $H_2O$ distilled deionized: 5 gm
   Silicone Emulsion Surfactant 2270: 1 gm
   Orthogynol: 20 gm
III. Double wall spermicidal composition
   (a) outer wall (Column 6 ingredients)
      prepolymer resin F-202: 10 gm
      catalyst: 0.25 gm
      P. diisobutylphenoxy polyethoxyethanol: 0.80 gm
   (b) Inner wall facing cervix (Column 7 ingredients)
      Hypol 2001: 50 gm
      $H_2O$ distilled deionized: 55 gm
      Silicone Emulsion Surfactant 2270: 4 gm
      P. diisobutylphenoxy polyethoxyethanol: 6.6 gm
      Sodium Carboxymethyl Cellulose: 1.6 gm
      Methyl Paraben: 0.15 gm
      Propylene Glycol: 15.0 gm
IV. Double wall spermicidal composition identical for both sides (Column 13 ingredients)
   Hypol 2001: 10 gm
   $H_2O$ distilled deionized: 5 gm
   Silicone Emulsion Surfactant 2270: 1 gm
   Conceptrol: 20 gm Formulae Table (in grams)

| Ingredients | Manufacturer | 1 | 2 | 3 | 4 | 5 | 6 | 7 | 8 | 9 | 10 | 11 | 12 | 13 |
|---|---|---|---|---|---|---|---|---|---|---|---|---|---|---|
| Hypol 2001 | Grace | 10 | 10 | | 10 | | | 50 | 50 | 50 | 10 | 10 | 10 | 10 |
| F-202 Prepolymer | Stephan | | | | | 10 | 10 | | | | | | | |
| Catalyst | *** | | | | | 0.25 | 0.25 | | | | | | | |
| $H_2O$ Distilled/Deionized | * | 10 | 10 | 10 | 10 | | | 55 | 28.5 | 40 | 5 | 5 | 5 | 5 |
| Silicone Emulsion Surfactant 2270 | Goldschmidt | 1 | 1 | 1 | 1 | | | 4 | 4 | 4 | 1 | | 1 | 1 |
| Nonoxynol 9 | * | 0.55 | | | | | | | | 0.6 | | | | |
| Dodecaethyleneglycol monolaurate | * | | 0.55 | | | 0.8 | | | | | | | | |
| Octoxynol | * | | | 0.55 | | | | | | | | | | |
| P. diisobutylphenoxy polyethoxyethanol | * | | | | 0.55 | | 0.8 | 6.6 | | | | | | |
| Sodium Carboxymethyl Cellulose | * | | | | | | | 1.6 | | | | | | |
| Methyl Paraben | * | | | | | | | 0.15 | 0.125 | | | | | |
| Propylene Glycol | * | | | | | | | 15 | 6 | | | | | |
| Stearyl Alcohol | * | | | | | | | | 12.5 | | | | | |
| Propyl Paraben | * | | | | | | | | 12.5 | | | | | |
| White Petroleum | * | | | | | | | | .0095 | | | | | |
| Sodium Lauryl Sulfate | * | | | | | | | | 0.5 | | | | | |
| Koromex Spermicide | Julius Schmidt | | | | | | | | | | | ** | | ** |
| Delfen | Ortho Pharma | | | | | | | | | | 10 | | | |
| Orthogynol | Ortho Pharma | | | | | | | | | | | 10 | 20 | |
| Conceptrol | Ortho Pharma | | | | | | | | | | | | | 20 |

*generic chemicals
**Koromex can be substituted for orthogynol or conceptrol
*** Catalyst composition (100%) : $H_2O$ 66.6%; triethanolamine 20.8%; triethylenediamine 12.6%

The medicament is activated by water before use. Examples of typical spermicidal compositions compatible with the foam technology of the present invention are given in the following table in which each of the 13 numerals corresponds to a specific formulation with the manufacturer's name wherever applicable. Separate

We claim:
1. A method of manufacturing a disposable contraceptive intravaginal cervical barrier, which comprises
   (a) assembling in sequence
      a first sheet of foam plastic,
      a plastic ring having the substantial shape of the circumference of said barrier, a layer of medicated gel, and a second flexible sheet, said first and second sheets being made of thermoformable material, (b) molding the assembly between a pair of heated dies for a sufficient time to form said assembly to the preselected shape of said dies, and (c) sealing said assembly.

2. The method of claim 1 wherein said medicated gel includes a medicament selected from the group consisting of spermicides, germicides, abortion inducing agents and combinations thereof.

3. The method of claim 1 further comprising the step of assembling in sequence after said second sheet, a third sheet comprised of foam plastic.

4. The method of claim 3, further comprising the step of assembling in sequence between said first sheet and said plastic ring a fourth sheet of plastic thermoformable film impermeable to the passage of sperm.

5. The method of claim 1, further comprising the step of assembling in sequence between said first sheet and said layer of gel a third sheet comprised of flexible film material permeable to the passage of water.

6. The method of claim 5, further comprising the step of assembling in sequence after said second sheet a fourth sheet made of plastic foam material.

7. A method of manufacturing a disposable contraceptive barrier, which comprises (a) mixing a liquid medicament into a liquid foam plastic material to form a mixture, (b) allowing said mixture to reach foaming temperature, (c) forming said mixture to the preselected shape of said cervical barrier, and thereafter (d) curing the mixture to a substantially resilient permanent shape.

8. The method of claim 7, further comprising the step of applying a first layer of resilient film material to said barrier after said mixture has cured.

9. The method of claim 8, further comprising the step of forming a second layer of liquid mixture of foam and medicament over said first layer of film after said first layer of film has cured.

10. The method of claim 7, further comprising the step of curing one side of said barrier to a sperm impermeable state.

11. The method of claim 7, further comprising the step of forming a rim on said barrier and curing the rim to a resilient state.

12. The method of claim 7 wherein said liquid medicament is selected from the group consisting of spermicides, germicides, abortion including agents and combinations thereof.

* * * * *